United States Patent [19]

Mori

[11] 4,453,967
[45] Jun. 12, 1984

[54] HOMOBRASSINOLIDE COMPOUNDS WHICH ARE STEROIDS HAVING PLANT GROWTH PROMOTING ACTIVITY

[75] Inventor: Kenji Mori, Tokyo, Japan

[73] Assignees: Sumitomo Chemical Company, Limited, Osaka; Earth Chemical Company, Limited, Hyogen, both of Japan

[21] Appl. No.: 422,487

[22] Filed: Sep. 23, 1982

Related U.S. Application Data

[63] Continuation of Ser. No. 264,045, May 15, 1981, abandoned.

[30] Foreign Application Priority Data

May 16, 1980 [JP] Japan .................................. 55/65602

[51] Int. Cl.³ .................... C07D 313/10; A01N 43/22
[52] U.S. Cl. ........................................ 71/88; 549/268
[58] Field of Search ............................ 549/268; 71/88

[56] References Cited

U.S. PATENT DOCUMENTS 4,346,226  8/1982  Thompson et al. ................. 549/268

OTHER PUBLICATIONS

Thompson et al., J. Org. Chem., vol. 44, No. 26, 1979, pp. 5002–5004.
Steffens, CA 92:123170n.
C & EN Nov. 5, 1979, p. 20.

*Primary Examiner*—Jane T. Fan
*Attorney, Agent, or Firm*—Birch, Stewart, Kolasch & Birch

[57] ABSTRACT

Homobrassinolide of the formula:

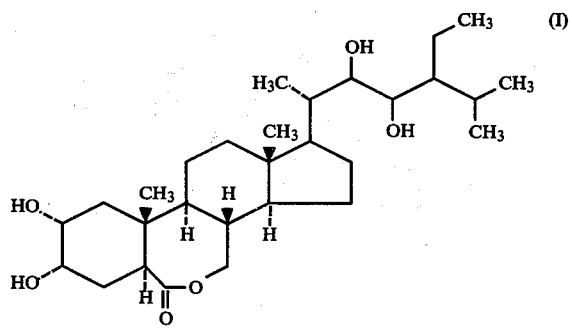

which shows a plant growth promoting activity.

2 Claims, No Drawings

HOMOBRASSINOLIDE COMPOUNDS WHICH ARE STEROIDS HAVING PLANT GROWTH PROMOTING ACTIVITY

This application is a continuation of copending application Ser. No. 264,045, filed on May 15, 1981, now abandoned.

The present invention relates to homobrassinolide and its synthesis. More particularly, it relates to the synthesis of homobrassinolide from stigmasterol, and the products of such synthesis.

In recent years, a certain steroid named "Brassinolide" having a plant growth promoting activity was isolated from the pollen of Brassica napus L., and the following chemical structure was assigned thereto [Chem. & Eng. News, Nov. 5, 20 (1979)]:

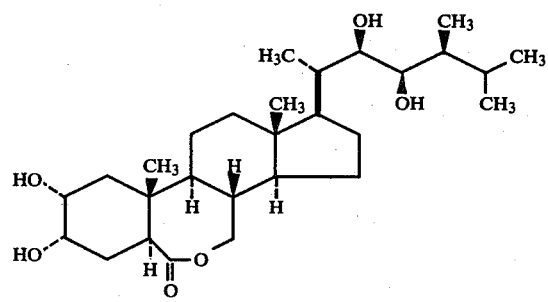

Subsequently, the synthesis of the structural isomers of the said brassinolide was achieved [J. Org. Chem., 44, 5002 (1979)], but this synthesis requires many and troublesome steps starting from ergosterol (i.e. ergosta-5,7,22-trien-3β-ol) and affords the objective structural isomers of brassinolide only in a yield of about 10%. In addition, those steps include the reaction which will take an extremely long time such as two weeks.

As a result of an extensive study, a compound of the formula:

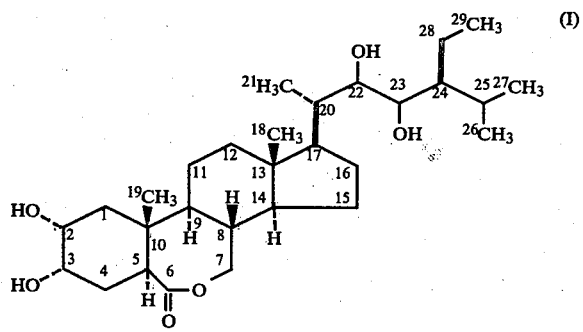

has newly been synthesized from stigmasterol (i.e. stigmasta-5,22-dien-3-ol) and found to exhibit a notable plant growth promoting activity. Since this compound is considered as a homologue to brassinolide in having one additional methyl group at the 29-position, we call it "homobrassinolide". Advantageously, the homobrassinolide can be produced from stigmasterol in several steps in good yields.

According to the present invention, the homobrassinolide can be synthesized as shown in the following scheme wherein R is an alkanesulfonyl group (e.g. methanesulfonyl), a benzenesulfonyl group or a alkylbenzenesulfonyl group (e.g. p-toluenesulfonyl) and R' is an acyl group such as lower alkanoyl (e.g. acetyl, propionyl, butyryl):

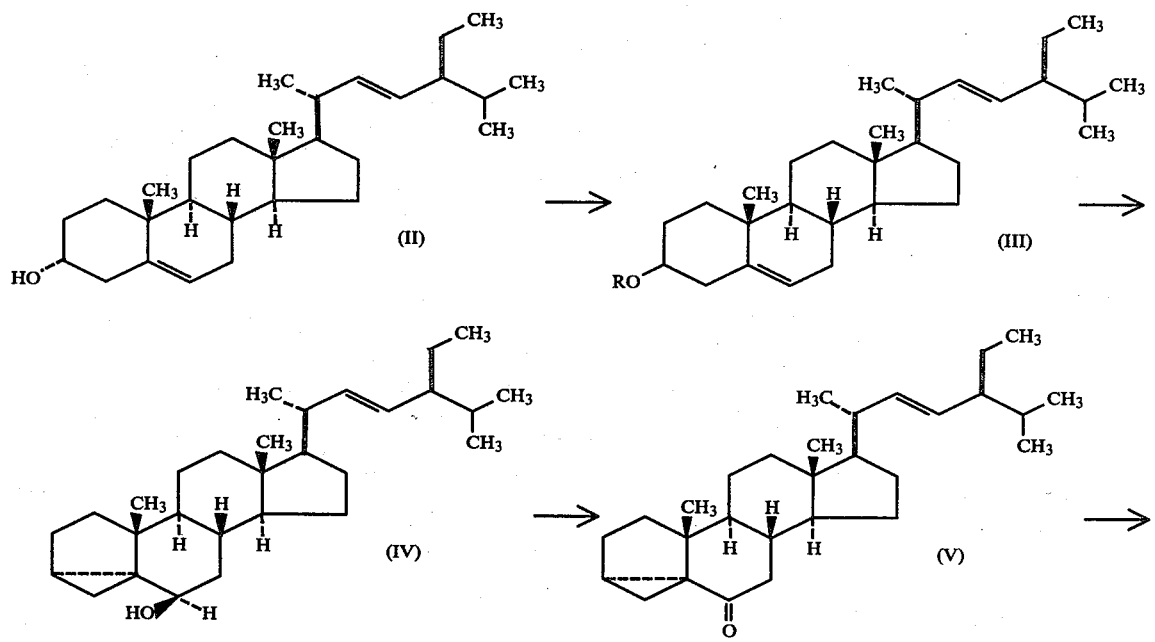

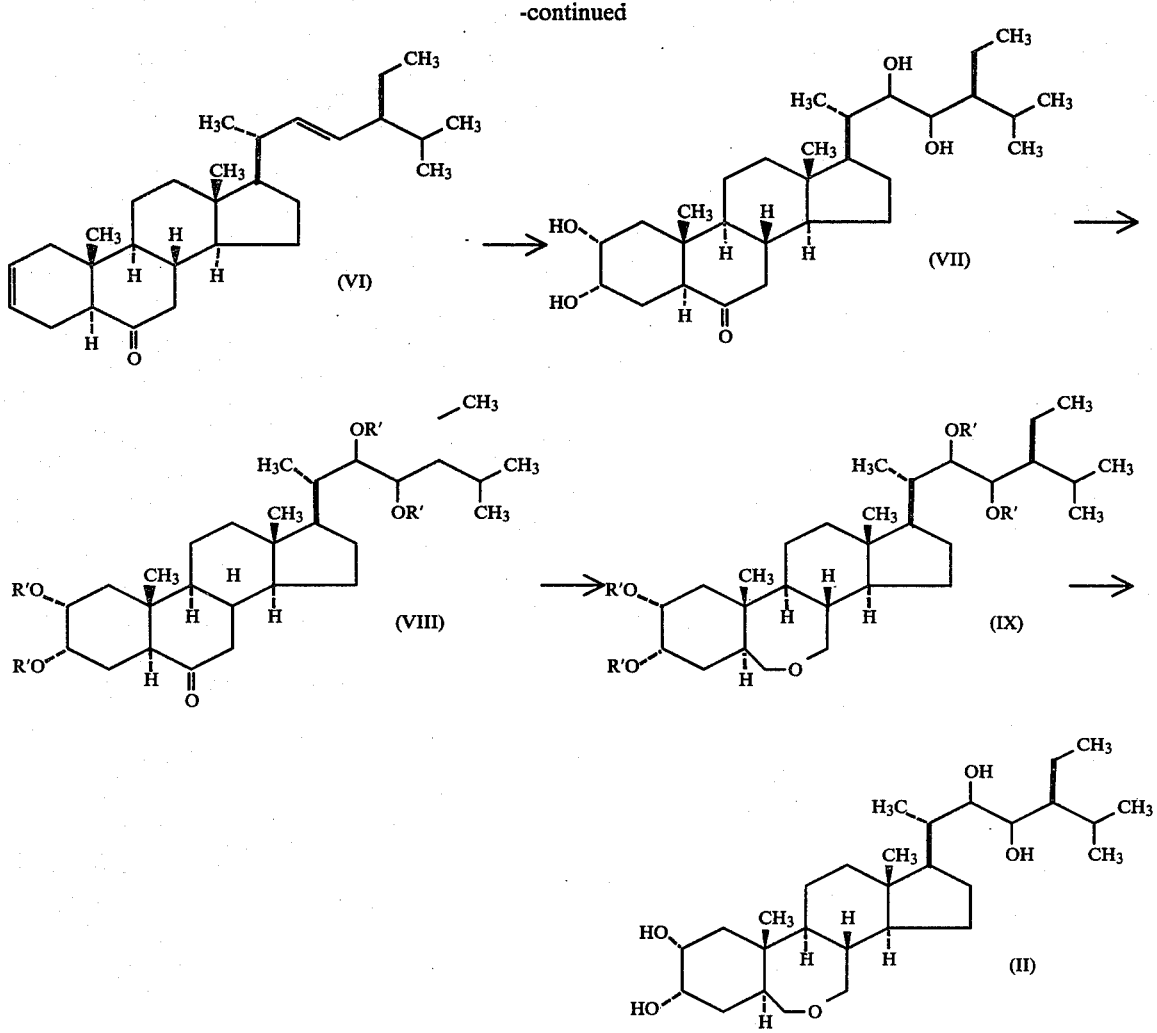

Explaining the above synthetic route, the starting stigmasterol (II) is a well known steroidal compound [J.Am.Chem.Soc., 62, 2006 (1940)].

In the first step, stigmasterol (II) is sulfonylated to its sulfonylated derivative (III). The sulfonylation may be effected by a per se conventional procedure, e.g. treating with a sulfonylating agent such as methanesulfonyl chloride, benzenesulfonyl chloride or p-toluenesulfonyl chloride in the presence of a base such as pyridine, triethylamine or dimethylaniline, usually in an inert solvent such as benzene, toluene or ether at a temperature of from −30° C. to the refluxing temperature.

In the second step, the sulfonylated derivative (III) is subjected to solvolysis to give i-stigmasterol (IV). The solvolysis may be carried out by treatment of the sulfonylated derivative (III) with an acid acceptor (e.g. sodium carbonate, sodium bicarbonate, potassium carbonate, potassium bicarbonate) in an aqueous medium such as a mixture of water and acetone.

The reactions in the above first and second steps are already known [J.Org.Chem., 28, 571 (1963)].

In the third step, i-stigmasterol (IV) is oxidized to the 6-keto compound (V). The oxidation may be carried out by the so-called Jones oxidation [e.g. W. Carruthers: "Some Modern Methods of Organic Synthesis", Cambridge University Press, 244 (1977)], e.g. treating with chromic anhydride, usually in an inert solvent (e.g. acetone, methylethylketone, diethylketone) under an acidic condition.

In the fourth step, the 6-keto compound (V) is subjected to rearrangement to give the 2,22-unsaturated compound (VI). The rearrangement can be carried out analogously to the process described in the literature [J.Org.Chem. (Communications), 44, 5002 (1979)], i.e. by treatment with an acidic substance (e.g. p-toluenesulfonic acid) is an inert solvent (e.g. sulfolane) at a rather elevated temperature, or by heating it in quinoline, for a period of 30 minutes to several hours. The treatment is preferably effected in an inert gas atmosphere such as argon.

In the fifth step, the 2,22-unsaturated compound (VI) is oxidized to the 2,3,22,23-tetraol compound (VII). The oxidation may be accomplished by catalytic osmylation [Tetrahedron Letters, 23, 1973 (1976)], preferably together with a tertiary amine N-oxide (e.g. N-methylmorpholine-N-oxide, pyridine-N-oxide) in an inert solvent (e.g. aqueous tetrahydrofuran, aqueous dioxane). The performance of the oxidation in an inert gas atmosphere such as argon is usually favorable. In general, the amount of osmium tetroxide may be much smaller than the theoretical amount, e.g. about 1/20 mol to 1 mol of the double bond in the 2,22-unsaturated compound (VI).

In the sixth step, the 2,3,22,23-tetraol compound (VII) is converted into the corresponding acylated derivative (VIII). The conversion may be accomplished by a per se conventional acylation procedure, e.g. treatment with acetic anhydride in the presence of a base (e.g. pyridine, dimethylaniline, dimethylaminopyridine, triethylamine).

In the seventh step, the acylated derivative (VIII) is subjected to oxidative ring expansion to give the homobrassinolide acylate (IX). The oxidative ring expansion can be achieved according to the so-called Baeyer-Villiger reaction [e.g. A. Streitwieser, Jr. et al.: "Introduction to Organic Chemistry", Macmillan Publishing Co., Inc., 391 (1976)], e.g. treatment with an organic peroxide such as trifluoroperacetic acid or m-chloroperbenzoic acid.

In the last step, the homobrassinolide acylate (IX) is deacylated to the homobrassinolide (I). The deacylation can be effected by a per se conventional hydrolysis procedure, e.g. treatment with an alkali (e.g. potassium hydroxide, sodium hydroxide), followed by treatment with a dilute mineral acid (e.g. dilute hydrochloric acid, dilute sulfuric acid). The treatment is usually made in an inert solvent such as an alkanol (e.g. methanol, ethanol) or dimethylsulfoxide.

The products in any of the above steps may be subjected to the reactions without isolation from the reaction mixture. However, the products are preferably isolated from the reaction mixture and purified by a per se conventional refining procedure such as solvent extraction, recrystallization, filtration, column chromatography or thin layer chromatography prior to the use in the subsequent step.

As mentioned above, the synthesis of the homobrassinolide (I) can be readily accomplished from easily available stigmasterol in several steps, which do not require any troublesome operation or a long reaction time. Advantageously, the homobrassinolide (I) is obtainable in good yields.

The homobrassinolide (I) shows a notable plant growth promoting activity and is useful as a plant growth promoter. For such use, it may be formulated in any preparation form conventionally employed in the agrochemical field. Namely, it may be admixed with solid or liquid carriers or diluents (e.g. mica, talc, clay, diatomaceous earth, water) to make powders, granules, tablets, pellets, solutions, dispersions, suspensions, etc. When desired, auxiliary agents such as emulsifiers may be also incorporated therein.

Application of the said preparation may be effected by a conventional procedure such as spraying, spreading, coating or dipping onto plants (e.g. leaf, stem, fruit, seed) or soils. The amount of the active ingredient to be applied is varied with preparation forms, kinds of plants to be treated, application methods, application times, etc. In general, the concentration of the active ingredient on the application may be not less than 0.05 ppm, preferably from 1 to 100 ppm. For perfusion of the rice fields therewith, its use in a daily amount of 10 to 1000 liters per 1000 m$^2$ with intervals of several days is advisable.

By the application of the homobrassinolide (I), various useful crop plants including rice, soybean, azuki bean, mung bean, wheat, tomato, cucumber, raddish, carot, lettuce, orange, apple, grape, etc. are promoted in their growth so that the cultivation period is shortened with improvement of the yield and quality of the crop plants. No injury is caused to those crop plants. When desired, it may be applied together with other growth promoters, fertilizers, herbicides, insecticides, etc.

Practical and presently preferred embodiments of this invention are illustratively shown in the following examples.

Example 1

Preparation of stigmasteryl tosylate (III: R=tosyl)

p-Toluenesulfonyl chloride (18.0 g) crystallized from petroleum ether (b.p. 60°–70° C.) was added to a solution of stigmasterol (15.0 g) in dry pyridine (200 ml), and the resultant mixture was allowed to stand overnight in a dark place. The reaction mixture was added to a 5% potassium bicarbonate solution (1 liter), and the precipitate was collected by filtration, washed with water and dried at 60° C. under reduced pressure. Recrystallization from anhydrous acetone gave stigmasteryl tosylate as colorless crystals. M.P. 147°–148° C. $[\alpha]_D = -49°$.

Example 2

Preparation of i-stigmasterol (IV)

Stigmasteryl tosylate (5.5 g) as obtained above and potassium bicarbonate (3.2 g) were dissolved in acetone (2 liters), water (200 ml) was added thereto, and the resultant mixture was refluxed for 6 hours. The reaction mixture was concentrated to a volume of 700 ml, diluted with water and extracted with ether. The ether extract was washed with water, dried over potassium carbonate and concentrated under reduced pressure to give a colorless oil (3.9 g). The oil was charged on a column with Florisil (150 g) and eluted with a mixture of petroleum ether and benzene (2:3 by weight) (250 ml) to give i-stigmasterol (3.0 g) as a colorless oil. Crystallization from a mixture of acetone and water gave colorless crystals. M.P. 48°–50° C. The product after purification by recrystallization from a mixture of water and acetone showed M.P. 50°–52° C. and $[\alpha]_D = +24°$.

Example 3

Preparation of 24S-ethyl-3α,5-cyclo-5α-cholest-22-en-6-one (V)

To a solution of i-stigmasterol (6.0 g) in acetone (100 ml) cooled with ice, 8N chromic acid (4 ml) was added, and the resultant mixture was stirred for 5 minutes. A small amount of methanol was added to the reaction mixture to decompose excessive chromic acid. After evaporation of acetone under reduced pressure, the residue was poured into a mixture of water and ether. The ether layer was separated, washed with water, a sodium bicarbonate solution and a saturated sodium chloride solution in order and dried over magnesium sulfate. After filtration, the filtrate was concentrated, and the residue was crystallized from 99% ethanol to give 24S-ethyl-3α,5-cyclo-5α-cholest-22-en-6-one (4.8 g) as needles. M.P. 98°–99° C. Yield 80%. The purified product after recrystallization from ethanol showed M.P. 102°–103° C. and $[\alpha]_D^{21} = +19.5°$ (c=8.000, CHCl$_3$).

IR: $\nu_{max}^{Nujol} = 1685(s)$, 1310(m), 1300(s), 1250(w), 1220(w), 1200(w), 1170(m), 1150(m), 1130(m), 1120(m), 1075(w), 1055(w), 1040(w), 1020(w), 1005(w), 970(s), 925(w), 920(w), 895(w), 870(w), 840(w), 810(w), 780(w), 720(w) cm$^{-1}$.

NMR: δ (60 MHz, CDCl$_3$)=0.73, 0.80, 0.86, 0.90, 1.02, 1.10 (18H, CH$_3$), 1.1–2.7 (26H, CH$_2$, CH), 5–15 (2H) ppm.

Elementaly analysis: Calcd. for C$_{29}$H$_{45}$O: C, 84.81%; H, 11.29%. Found: C, 85.41%; H, 11.44%.

Example 4

Preparation of 24S-ethyl-5α-cholesta-2,22-dien-6-one (VI)

To a solution of 24S-ethyl-3α,5-cyclo-5α-cholest-22-en-6-one (3.5 g) as obtained above in sulfolane (25 ml), p-toluenesulfonic acid (180 mg) was added, and the resultant mixture was heated at 160° C. in argon atmosphere for 70 minutes. After cooling, water was added to the reaction mixture, followed by extraction with a mixture of benzene and toluene (1:1 by weight). The extract was washed with water and a saturated sodium chloride solution, dried over magnesium sulfate and filtered. The filtrate was concentrated under reduced pressure, and the residue was purified by chromatography on silica gel (Kieselgel 60, 70–230 mesh, 35 g, n-hexane). From the eluate with a mixture of n-hexane and benzene (1:1 by weight), there was obtained 24S-ethyl-5α-cholesta-2,22-dien-6-one (2.3 g). Yield 66%. Recrystallization from 99% ethanol gave prisms. M.P. 111°–112° C. [α]$_D^{21}$=+18.4° (c=1.151, CHCl$_3$).

IR: ν$_{max}^{Nujol}$=3020(m), 1705(s), 1650(w), 1330(w), 1310(w), 1300(w), 1285(w), 1260(m), 1230(m), 1190(w), 1180(w), 1160(w), 1120(w), 1100(w), 1070(m), 1045(w), 1020(w), 995(m), 965(s), 940(w), 870(w), 845(w), 815(w), 780(w), 750(w), 720(w), 670(m) cm$^{-1}$.

NMR: δ (60 MHz, CDCl$_3$)=0.69, 0.78, 0.84, 0.88, 0.96, 1.08 (18H, CH$_3$), 1.1–2.5 (24H, —CH$_2$, —CH—), 5.10 (2H), 5.60 (2H, br.s) ppm.

Elementary analysis: Calcd. for C$_{29}$H$_{45}$O: C, 84.81%; H, 11.29%. Found: C, 85.19; H, 11.60%.

Example 5

Preparation of 2α,3α,22,23-tetrahydroxy-24S-ethyl-5α-cholestan-6-one (VII)

To a solution of 24S-ethyl-5α-cholesta-2,22-dien-6-one (4.0 g) as obtained above in tetrahydrofuran (80 ml), a solution of osmium tetroxide (210 mg) in t-butanol (7 ml), N-methylmorpholine-N-oxide (3 g) and water (20 ml) were added, and the resultant mixture was stirred at room temperature in argon atmosphere for 2 days. N-Methylmorpholine-N-oxide (1 g) was added thereto. The resulting mixture was stirred for 1 day, and N-phenylmorpholine-N-oxide (1 g) was again added thereto, followed by stirring for 1 day. The reaction mixture was shaken with a solution of sodium hydrosulfite (2 g) in water (4 ml) for reduction of osmium tetroxide to osmium and filtered through a layer of Celite. The filtrate was concentrated and admixed with chloroform and dilute hydrochloric acid. The chloroform layer was separated, dried over potassium carbonate and concentrated. The residue was crystallized from a mixture of ether and petroleum ether to precipitate 2α,3α,22,23-tetrahydroxy-24S-ethyl-5α-cholestan-6-one (2.4 g). Yield 52%. Recrystallization from 99% ethanol gave prisms. M.P. 143°–148° C. (sintering); 200°–210° C. (melting). [α]$_D^{21}$=−1.9° (c=1.294, CHCl$_3$).

IR: ν$_{max}^{Nujol}$=3350(s), 1715(s), 1340(m), 1320(m), 1310(m), 1280(m), 1250(m), 1240(m), 1230(m), 1205(w), 1180(w), 1150(w), 1115(m), 1100(m), 1080(s), 1065(s), 1055(s), 1050(s), 1035(s), 1010(s), 1000(m), 990(m), 965(w), 940(w), 930(w), 900(w), 870(w), 840(w), 790(w), 780(w), 750(w), 720(w), 700(w) cm$^{-1}$.

Elementary analysis: Calcd. for C$_{29}$H$_{50}$O$_5$: C, 72.76%; H, 10.53%. Found: C, 73.03%; H, 11.17%.

Example 6

Preparation of 2α,3α,22,23-tetracetoxy-24S-ethyl-5α-cholestan-6-one (VIII)

To a solution of 2α,3α,22,23-tetrahydroxy-24S-ethyl-5α-cholestan-6-one (380 mg) obtained as above in dry pyridine (3 ml), acetic anhydride (1 ml) and 4-(N,N-dimethylamino)pyridine (0.1 g) were added, and the resultant mixture was allowed to stand at room temperature overnight. The reaction mixture was admixed with ice and dilute hydrochloric acid and extracted with ether. The ether extract was washed with water, a sodium bicarbonate solution and a saturated sodium chloride solution in order, dried over magnesium sulfate and concentrated. The residue was purified by chromatography on silica gel (5×1.5 cm, Kieselgel 60, 70–230 mesh, n-hexane). From the fraction eluted with a mixture of n-hexane and ethyl acetate (9:1–4:1 by weight), there was obtained 2α,3α,22,23-tetracetoxy-24S-ethyl-5α-cholestan-6-one (500 mg). Yield 95%. The above product was an isomeric mixture of the (22R,23R) isomer and the (22S,23S) isomer in a gummy state.

IR: ν$_{max}^{film}$=1740(s), 1705(s), 1230(s), 1170(m), 1150(m), 1100(w), 1070(w), 1030(m), 1010(m), 980(w), 965(w), 940(w), 915(w), 890(w), 875(w) cm$^{-1}$.

Example 7

Preparation of 2α,3α,22,23-tetracetoxy-24S-ethyl-B-homo-7-oxa-5α-cholestan-6-one (IX)

To a solution of 2α,3α,22,23-tetracetoxy-24S-ethyl-5α-cholestan-6-one (598 mg) in dry dichloromethane (30 ml), pulverized sodium hydrogen phosphate (3 g) was added, followed by stirring. Separately, anhydrous trifluoroacetic acid (3.3 ml) was added to a suspension of 90% hydrogen peroxide (0.5 ml) in dichloromethane (5 ml) and shaken while cooling with ice to make a peracid solution. The peracid solution was dropwise added to the said mixture under stirring, whereby heat was generated. After completion of the heat generation, stirring was continued under reflux for 1.5 hours. After cooling, ice water was added to the reaction mixutre, the water layer was extracted with dichloromethane. The dichloromethane extract was combined with the dichloromethane layer, washed with a sodium bicarbonate solution, dried over magnesium sulfate and concentrated. The residue was purified by chromatography on silica gel (Mallinckrodt Silicar cc-7, 20×1.6 cm, n-hexane). From the fraction eluted with a mixture of n-hexane and ethyl acetate (9:1–4:1 by weight), there was obtained 2α,3α,22,23-tetracetoxy-24S-ethyl-B-homo-7-oxa-5α-cholestan-6-one (405 mg). Yield 66%. M.P. 174°–178° C. Recrystallization from a mixture of ethyl acetate and petroleum ether gave rods. M.P. 176°–178° C. [α]$_D^{20}$=+24.4° (c=1.006, CHCl$_3$).

IR: ν$_{max}^{Nujol}$=1740(s), 1720(s), 1330(w), 1315(w), 1305(w), 1250(s), 1225(s), 1180(m), 1170(w), 1125(w), 1115(w), 1050(sh), 1040(m), 1015(m), 960(w), 940(w), 915(w), 900(w), 890(w), 875(w), 765(w), 720(w) cm$^{-1}$.

NMR: δ (60 MHz, CDCl$_3$)=0.6–1.1 (18H, CH$_3$, 0.70, 0.79, 0.89, 0.98), 2.00 (3H, s), 2.07 (3H, s), 2.10 (6H, s), 3.0 (1H, m, CHC=O), 4.10 (2H, d, J=5 Hz, —CH$_2$O—), 4.70–5.50 (4H, —CHOAc, 4.8, 5.02, 5.2, 5.35) ppm.

Elementary analysis: Calcd. for C$_{37}$H$_{58}$O$_{10}$: C, 67.04%; H, 8.82%. Found: C, 66.93%; H, 8.86%.

Example 8

Preparation of 2α,3α,22,23-tetracetoxy-24S-ethyl-B-homo-7-oxa-5α-cholestan-6-one (IX)

To a solution of 2α,3α,22,23-tetracetoxy-24S-ethyl-5α-cholestan-6-one (9.0 g) in chloroform (100 ml), m-chloroperbenzoic acid (4.9 g) was added, and p-toluenesulfonic acid monohydrate (0.1 g) was added thereto, followed by stirring at room temperature for 5 days. The reaction mixture was poured onto ice water (300 ml) and extracted with chloroform (300 ml). The chloroform extract was washed with a sodium sulfite solution, a sodium bicarbonate solution and a saturated sodium chloride solution in order, dried over magnesium sulfate and concentrated. The residue (9 g) was purified by column chromatography on silica gel (200 g). From the fraction eluted with a mixture of n-hexane and ethyl acetate (10:1–3:1 by weight), there was obtained 2α,3α,22,23-tetracetoxy-24S-ethyl-3-homo-7-oxa-5α-cholestan-6-one (2 g).

Example 9

Preparation of 2α,3α,22,23-tetracetoxy-24S-ethyl-B-homo-7-oxa-5α-cholestan-6-one (IX)

A mixture of 30% hydrogen peroxide (15 ml) and chloroform (50 ml) was cooled to 0°–5° C., anhydrous trifluoroacetic acid (35 ml) was dropwise added thereto in about 20 minutes, and stirring was continued for 30 minutes. To the resultant trifluoroperacetic acid solution, a solution of 2α,3α,22,23-tetracetoxy-24S-ethyl-5α-cholestan-6-one (4.6 g) in methylene chloride (150 ml) was added at 0°–5° C. in about 30 minutes. After the addition was completed, the temperature was elevated to about 20° C., and stirring was continued for 1 hour. The organic solvent layer was separated, washed with a saturated sodium sulfite solution, a saturated sodium bicarbonate solution and a saturated sodium chloride solution in order, dried over magnesium sulfate and concentrated. The residue (4 g) was purified by column chromatography on silica gel (80 g). From the fraction eluted with a mixture of n-hexane and ethyl acetate (3:1 by weight), there was obtained 2α,3α,22,23-tetracetoxy-24S-ethyl-B-homo-7-oxa-5α-cholestan-6-one (3 g).

Example 10

Preparation of 2α,3α,22,23-tetrahydroxy-24S-ethyl-B-homo-7-oxa-5α-cholestan-6-one (I)

To a solution of 2α,3α,22,23-tetracetoxy-24S-ethyl-B-homo-7-oxa-5α-cholestan-6-one (250 mg) in methanol (6 ml), a solution of sodium hydroxide (500 mg) in water (1 ml) was added, and the resultant mixture was refluxed under stirring for 1 hour. After stirring at room temperature for additional 1 hour, tetrahydrofuran (6 ml) was added thereto, and 6 N hydrochloric acid (3 ml) was introduced therein to make acidic, followed by refluxing and stirring for 30 minutes. The reaction mixture was concentrated under reduced pressure to eliminate tetrahydrofuran and methanol, a small amount of sodium hydrogen carbonate was portionwise added thereto to make neutral and the resultant mixture was extracted with trichloromethane. The extract was dried over magnesium sulfate, filtered and concentrated to give 2α,3α,22,23-tetrahydroxy-24S-ethyl-B-homo-7-oxa-5α-cholestan-6-one (130 mg). Yield 70%. Recrystallization from methanol gave needles. M.P. 186°–188° C. [α]$_D^{20}$ = +35.6° (c=0.54, CHCl$_3$).

IR: $\nu_{max}^{Nujol}$ = 3400(br.s), 1730(sh), 1710(sh), 1695(s), 1405(m), 1350(m), 1330(m), 1290(sh), 1280(m), 1270(sh), 1250(w), 1225(sh), 1220(m), 1190(m), 1180(m), 1160(w), 1130(m), 1120(m), 1100(w), 1065(s), 1020(m), 990(m), 965(w), 950(w), 930(w), 915(w), 880(w), 860(w), 835(w), 820(w), 770(w), 715(w) cm$^{-1}$.

NMR: δ (60 MHz, CDCl$_3$)=0.6–1.1 (18H, CH$_3$, 0.70, 0.78, 0187, 0.95), 1.1–2.5 (22H, CH$_2$, CH), 2.90 (2H), 3.55 (2H), 4.0 (2H, br. —CH$_2$O—) ppm.

$^{13}$C—NMR (CDCl$_2$—CD$_3$OD = 9/1): 177.86 (C=O) ppm.

Elementary analysis: Calcd. for C$_{29}$H$_{50}$O$_6$: C, 70.41%; H, 10.19%. Found: C, 70.71%; H, 10.29%.

Test Example 1

According to the lamina joint test as described in "Shokubutsu no Kagaku Chosetsu (Chemical Regulation on Plant)", 5, 67–72 (1970), the plant growth promoting activity of the homobrassinolide (I) was examined.

Namely, the seeds of rice were immersed in water at 30° C. for 2 days. The evenly germinated seeds were chosen and sowed in a vessel charged with sand. Cultivation was carried out under a dark condition at 30° C. for 7 days, during which red light was occasionally irradiated. When a third leaf appeard over the top of the second leaf, the second leaf was taken, and its sheath was cut in 20 cm long. The resulting leaf piece was fixed on a glass plate by the aid of an instantaneous bonding agent in such manner as could be inclined at a horizontal plane. The glass plate was immersed in the test solution or water in a Petri dish in such manner that the leaf piece was kept at the liquid surface. After immersion for 24 hours, the angle between the leaf blade and the leaf sheath (i.e. the piece inclination angle) was measured at 30° C. under irradiation with red light using a projecting tester manufactured by Toshiba Corporation and a rotary screen.

The test solution was prepared by dissolving the homobrassinolide (I) or indoleacetic acid (for comparison) in water and diluting the resulting solution with water to make a desired concentration within a range of 0.01 to 50 ppm. The increased inclination angle to the inclination angle of the leaf piece immersed in water (as control) is shown in Table 1 wherein each value indicates an average on 20 leaf pieces.

TABLE 1

| Test solution | Concentration (ppm) | Increased inclination angle (°) |
|---|---|---|
| Homobrassino- | 0.05 | 55 |
| lide (I) | 0.1 | 60 |
|  | 0.5 | 70 |
|  | 1 | 80 |
|  | 5 | 70 |
|  | 10 | 70 |
|  | 50 | 60 |
| Indoleacetic acid | 0.05 | — |
|  | 0.1 | — |
|  | 0.5 | — |
|  | 1 | 5 |

TABLE 1-continued

| Test solution | Concentration (ppm) | Increased inclination angle (°) |
| --- | --- | --- |
| | 5 | 30 |
| | 10 | 40 |
| | 50 | 55 |

As understood from Table 1, the homobrassinolide (I) shows a remarkable increased inclination angle even at a low concentration around 1 ppm. Indoleacetic acid, which is a well known plant growth promoter, shows no growth promoting activity at about 1 ppm and gives practical activity at a high concentration around 50 ppm. Thus, the homobrassinolide (I) produces the same effects as indoleacetic acid in a concentration of about 1/1000 that required to produce comparable effects with indoleacetic acid.

What is claimed is:

1. A compound of the formula:

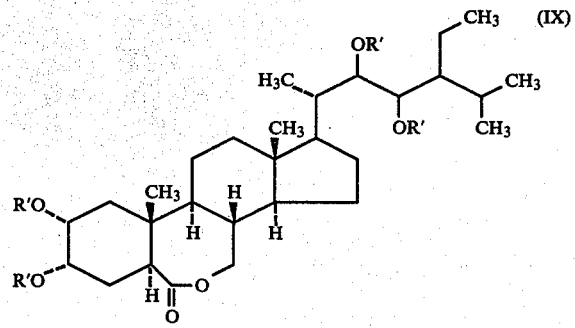

wherein R' is a lower alkanoyl.

2. A compound according to claim 1, wherein R' is a member selected from the group consisting of acetyl, propionyl and butyryl.

* * * * *